United States Patent
Gillerfalk et al.

[11] Patent Number: 5,948,247
[45] Date of Patent: Sep. 7, 1999

[54] DISINFECTION ARRANGEMENT FOR DIALYSIS MACHINES

[75] Inventors: Björn Gillerfalk; Sture Hobro, both of Lund; Jörgen Jönsson, Sjöbo; Erik Linderup, Lund, all of Sweden

[73] Assignee: Gambro AB, Sweden

[21] Appl. No.: 08/809,177

[22] PCT Filed: Jun. 6, 1995

[86] PCT No.: PCT/SE95/00649

§ 371 Date: May 28, 1997

§ 102(e) Date: May 28, 1997

[87] PCT Pub. No.: WO96/09080

PCT Pub. Date: Mar. 28, 1996

[30] Foreign Application Priority Data

Sep. 23, 1994 [SE] Sweden .................................. 9403201

[51] Int. Cl.$^6$ .............................. B01D 61/30; A61M 1/14
[52] U.S. Cl. .......................... 210/194; 210/175; 210/181; 210/195.1; 210/195.2; 210/321.66; 210/636
[58] Field of Search .................................... 210/636, 646, 210/175, 194, 195.1, 195.2, 321.69, 420, 181, 321.66; 422/1, 28, 38; 134/22.1, 22.11, 22.12

[56] References Cited

U.S. PATENT DOCUMENTS

| | | |
|---|---|---|
| 3,441,136 | 4/1969 | Serfass et al. . |
| 3,738,382 | 6/1973 | Cappelen, Jr. et al. . |
| 3,738,392 | 6/1973 | Veach et al. . |
| 4,018,684 | 4/1977 | Uffer ........................................ 210/140 |
| 4,122,010 | 10/1978 | Riede et al. ............................... 210/90 |
| 4,331,540 | 5/1982 | Witsoe ..................................... 210/646 |
| 4,399,030 | 8/1983 | Hlavinka et al. .......................... 210/91 |
| 4,728,496 | 3/1988 | Petersen et al. ..................... 210/321.72 |
| 4,774,415 | 9/1988 | Biegel et al. ......................... 210/455.1 |
| 5,032,265 | 7/1991 | Jha et al. .............................. 210/195.2 |
| 5,409,612 | 4/1995 | Maltais et al. .......................... 210/636 |
| 5,603,902 | 2/1997 | Maltais et al. .......................... 210/636 |
| 5,647,984 | 7/1997 | Hovland et al. ........................ 210/420 |

FOREIGN PATENT DOCUMENTS

| | | |
|---|---|---|
| 85/105660 | 5/1985 | European Pat. Off. . |
| 0208090 | 1/1987 | European Pat. Off. . |
| 2559241 | 7/1976 | Germany . |
| 3447989 | 1/1986 | Germany . |
| 61244372 | of 0000 | Japan . |
| 1579177 | 4/1977 | United Kingdom . |
| WO 93/09821 | 5/1993 | WIPO . |

Primary Examiner—John Kim
Attorney, Agent, or Firm—Lerner, David, Littenberg, Krumholz & Mentlik, LLP

[57] ABSTRACT

Apparatus for disinfecting dialysis devices are disclosed including a first circulation conduit for circulating a first fluid through at least a portion of the supply conduit to a dialyzer in order to disinfect that portion of the supply conduit and a second circulation conduit for circulating a second fluid through at least a portion of the removal conduit from the dialyzer for disinfecting that portion of the removal conduit.

23 Claims, 3 Drawing Sheets

DISINFECTION ARRANGEMENT FOR DIALYSIS MACHINES

FIELD OF THE INVENTION

The present invention relates to a disinfection apparatus for a dialysis machine. In particular the present invention relates to a heat disinfection apparatus for a hemodialysis machine, in which the disinfection occurs in two separate circuits, one for the clean side of the dialysis machine and one for the dirty side of the dialysis machine.

BACKGROUND OF THE INVENTION

A disinfection arrangement for a hemodialysis machine is described in German Patent Specification No. 34 47 989. This hemodialysis machine is provided with an inner shunt conduit which, in principle, connects the machine's used dialysis solution outlet with the inlet of the machine or, more specifically, a mixing chamber for the dialysis solution. A disinfectant is thus supplied to the dialysis machine and is made to circulate in the closed circuit through the machine and through the aforementioned shunt conduit. The disadvantage with this disinfection arrangement is that the same solution circulates on the clean side as well as on the dirty side of the dialysis machine. By the terminology "dirty side" of the machine is meant the side which, during normal operation, is positioned downstream of the dialyzer and contains the dialysis solution which comes from the dialyzer, which can contain blood plasma (ultrafiltrate).

Another disinfection arrangement for a dialysis machine is described in European Patent Application No. 208,090. This machine is provided with a shunt conduit which extends from a dialyzer coupling (the clean side of the dialyzer) to the inlet of the dialysis machine. In this manner, a recirculation circuit is formed which only includes the clean side of the dialysis machine. Additionally, a heating element is positioned in a water vessel in the recirculation circuit. The heating element is used to successively heat up the fluid, normally water, which is circulating in the circuit, to a high temperature, for example above 95° C. In this manner, a heated disinfection and/or sterilization is achieved. A small portion of the warm fluid is tapped off to the dirty side of the dialysis machine and passes therethrough, and out to the outlet, whereby the dirty side of the machine is also disinfected. The temperature of the fluid, however, falls during this passage, which results in the disinfection of the dirty side being less effective.

SUMMARY OF THE INVENTION

The object of the present invention is to achieve a disinfection arrangement corresponding to European Patent Application No. 208,090, but in which the dirty side is also effectively disinfected and/or sterilized.

Another object of the present invention is to provide a heat disinfection apparatus for a dialysis machine in which the required heat energy is used effectively.

In accordance with the present invention, these and other objects have now been accomplished by the invention of apparatus for disinfection of a dialysis device comprising a dialysis solution supply conduit for supplying dialysis solution to a dialyzer and a dialysis solution removal conduit for removing the dialysis solution from the dialyzer, the apparatus comprising first circulation means for circulating a first fluid through at least a portion of the dialysis solution supply conduit for disinfecting the at least a portion of the dialysis solution supply conduit and second circulation means for circulating a second fluid through at least a portion of the dialysis solution removal conduit for disinfecting the at least a portion of the dialysis solution removal conduit.

In accordance with one embodiment of the apparatus of the present invention, the second circulation means includes second fluid heating means for heating the second fluid.

In accordance with another embodiment of the apparatus of the present invention, the dialysis solution supply conduit includes first fluid heating means for heating the first fluid. In a preferred embodiment, the apparatus includes a heat exchanger for transferring heat between the first fluid in the first circulation means and the second fluid in the second circulation means.

In accordance with another embodiment of the apparatus of the present invention, the dialysis solution removal conduit includes an inlet associated with the dialyzer and an outlet, and the second circulation means comprises a second fluid conduit for recirculation of the second fluid from the outlet of the dialysis solution removal conduit to the inlet of the dialysis solution removal conduit. In a preferred embodiment, the apparatus includes a heat exchanger for transferring heat between the first fluid in the first circulation means and the second fluid in the second circulation means. In a particularly preferred embodiment, the heat exchanger is connected to the second fluid conduit.

In accordance with another embodiment of the apparatus of the present invention, the apparatus includes a shunt conduit for transferring fluid between the first circulation means and the second circulation means.

In accordance with another embodiment of the apparatus of the present invention, the dialysis solution supply conduit includes at least one disinfecting medium inlet for supplying a disinfecting medium to the dialysis solution supply conduit. In a preferred embodiment, the shunt conduit includes a pump.

Therefore, in accordance with this invention, there is provided a disinfection arrangement for a dialysis machine comprising a feed arrangement constituting a clean side of the dialysis machine, for normally supplying a dialysis solution to a dialyzer; a return arrangement constituting a dirty side of the dialysis machine for normally removing the dialysis solution from the dialyzer; and means for circulating a first fluid in a first recirculation circuit within the clean side of the dialysis machine for disinfection of the clean side of the dialysis machine.

According to the present invention, the disinfection arrangement comprises means for circulation of a second fluid in a separate second recirculation circuit within the dirty side of the dialysis machine, said second circuit comprising a heating arrangement.

The heating arrangement so utilized is preferably a heat exchanger arranged to transfer heat energy from the first circuit to the second circuit. Alternatively or additionally, a heating member can be included in the second circuit for heating the second fluid.

According to a preferred embodiment of the present invention, the disinfection arrangement comprises a recirculation conduit which connects the inlet of the return arrangement with its outlet for recirculation of the second heated fluid.

In another embodiment of the present invention, the disinfection arrangement comprises a shunt conduit between the first circuit and the second circuit for transfer of fluid from the first circuit to the second circuit.

BRIEF DESCRIPTION OF THE DRAWINGS

The invention will now be described in more detail with reference to the accompanying drawings which depict preferred embodiments of the invention, as follows.

DETAILED DESCRIPTION

Figure 1:
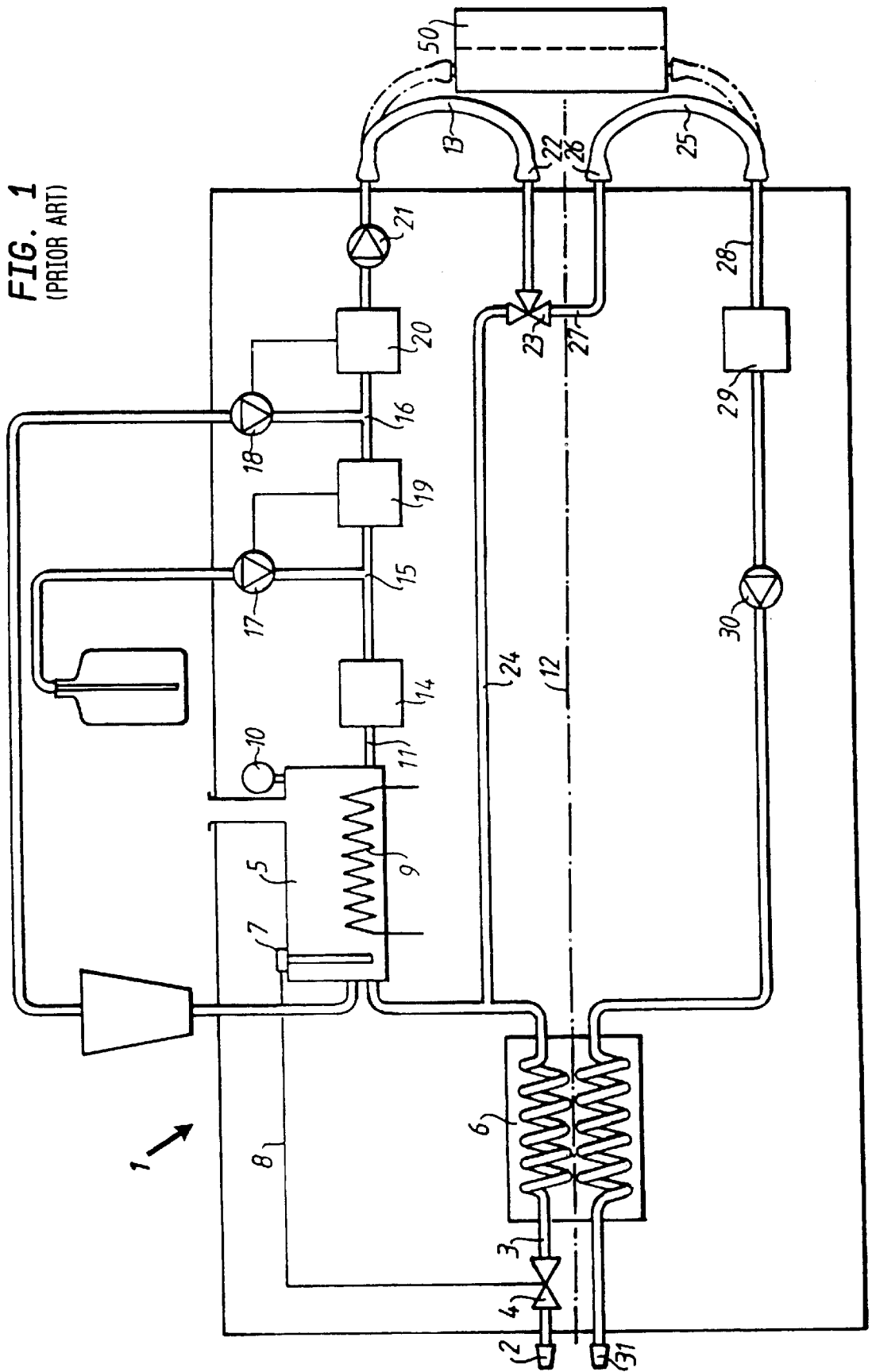
FIG. 1 is a schematic representation of a dialysis machine of the general type disclosed in European Patent Application No. 208,090.

Turning to the drawings, in which like reference numerals refer to like elements thereof, FIG. 1 shows a dialysis machine 1 substantially in accordance with European Patent Application No. 208,090. Several components of the dialysis machine which are not necessary for an understanding of the present invention have been omitted therefrom.

The dialysis machine 1 comprises an inlet 2 for clean water, which normally comes from a water purification unit (such as a reverse osmosis unit). The inlet 2 is connected to a water vessel 5 by means of an inlet conduit 3 and an inlet valve 4. A heat exchanger 6 may be located in the conduit 3, but this heat exchanger is in some machines only an accessory (i.e., it is optional).

The water vessel 5 is provided with a level detector 7 which controls the inlet valve 4 (indicated by line 8) so that the level in the water vessel 5 is substantially constant. The water vessel 5 is normally connected to the surrounding atmosphere as shown. Additionally, the water vessel comprises an immersion heater 9. A temperature sensor 10 detects the temperature of the water in the water vessel 5 and regulates the power supply to the immersion heater 9 so that the correct water temperature is attained, normally about 37° C.

A feed conduit 11 extends from the water vessel 5 to a tube 13 for connection to a dialyzer 50. The conduit 11 comprises various arrangements 14, such as a dearator device, pH-sensor, flow meter, and the like, as well as two mixing points 15 and 16. The water in the conduit 11 is mixed with a concentrate at the mixing point 15, which concentrate can be an A-concentrate (Acid-concentrate) by means of a metering pump 17. A B-concentrate (Bicarbonate-concentrate) is supplied at the second mixing point 16 by means of a metering pump 18. Supply of a substantially saturated bicarbonate solution from a cartridge filled with bicarbonate powder (BICART®) is shown in FIG. 1.

Additionally, there are measurement cells 19 and 20 in the conduit 11 in order to measure the conductivity of the mixture obtained. The measurement cells 19 and 20 control the metering pumps 17 and 18 so that the correct metering is obtained. The conduit 11 also comprises a pump 21 which ensures that a predetermined flow is maintained in the conduit 11, for example about 500 milliliters/minute.

The tube 13 is normally connected to the first side (the clean side) of the dialyzer 50. When no dialyzer is connected, the tube is instead connected with a bypass-conduit 27 by means of a coupling 22 as shown in FIG. 1. The coupling 22 is connected with a three-way valve 23, one end of which is connected to the water vessel 5 by means of a recirculation conduit 24.

The above-described portion of the dialysis machine (elements 2–24) constitute its clean side (only half of the heat exchanger 6), as indicated with dashed line 12.

The dialysis machine is connected with the other side (dirty side) of the dialyzer 14 by means of a tube 25. When the tube 25 is not connected to the dialyzer 50 it is connected with a coupling 26 which, in turn, is connected with the three-way valve 23 by means of the bypass-conduit 27. The other end of the tube 25 is connected with an outlet conduit 28 which comprises various arrangements 29, such as blood leakage detectors, flow meter devices, and the like, as well as a pump 30. The outlet conduit passes through the other side of the heat exchanger 6, if such is present, and to an outlet coupling 31.

During normal operation with the dialyzer 50 connected, the pumps 21 and 30 are operated according to a mutual relationship such that a desired pressure is maintained on the dialysis side of the membrane in the dialyzer 14 so that a desired ultrafiltration is obtained.

The portion of the dialysis machine described above with reference numerals 25–31 forms the dirty side of the dialysis machine below the dashed line 12 in FIG. 1.

When disinfecting the dialysis machine according to FIG. 1, the tubes 13 and 25 are placed in the position shown with solid lines, connected to the couplings 22 and 26, respectively. The valve 23 is adjusted so that substantially all of the solution flowing through tube 13 is recirculated through the conduit 24. The heating element 9 is activated and successively heats up the water which is circulating through the conduit 11, the tube 13, the valve 23, the conduit 24 and the water vessel 5 to a higher and higher temperature until the temperature reaches at: least 95° C., which is detected by the temperature sensor 10.

Then, the valve 23 is adjusted (or is already in a position) so that a certain portion of the water going through the tube 13 passes out through the shunt conduit 27, the tube 25, the conduit 28 and the connection 31 to the drain. The portion which passes through the shunt conduit 27 and to the drain is only a small portion, for example 10% of the amount which is circulating in the shunt conduit 24. Of course, valve 23 can be a three-way valve or a valve arrangement or combination having two distinct positions, one for normal operation and one for heat disinfection.

In this manner, the clean side of the dialysis machine will be heat-disinfected and/or sterilized while the dirty side of the machine is disinfected with water at successively lower temperatures towards the outlet 31. The level detector 7 in the water vessel 5 ensures that the level in the water vessel 5 is kept constant, which means that the valve 4 allows a small amount of water in, depending on how large the amount is which passes out through the outlet 31. Disinfection of the concentrate inlet at the pumps 17 and 18 also occurs, which is not explained in detail here. Disinfection occurs with pure water or with the addition of some disinfection medium, as well as possibly also decalcification medium, such as citric acid (CLEANCART®), in any suitable combination.

In accordance with the present invention it is desirable to also disinfect the dirty side of the dialysis machine to a greater extent than that which occurs in the dialysis machine according to FIG. 1. The dialysis machine according to FIG. 1 is therefore provided with a second separate recirculation circuit on the dirty side. Such an embodiment is shown on more detail in FIG. 2. The same components as in FIG. 1 have been given the same reference numerals in FIG. 2.

Figure 2:
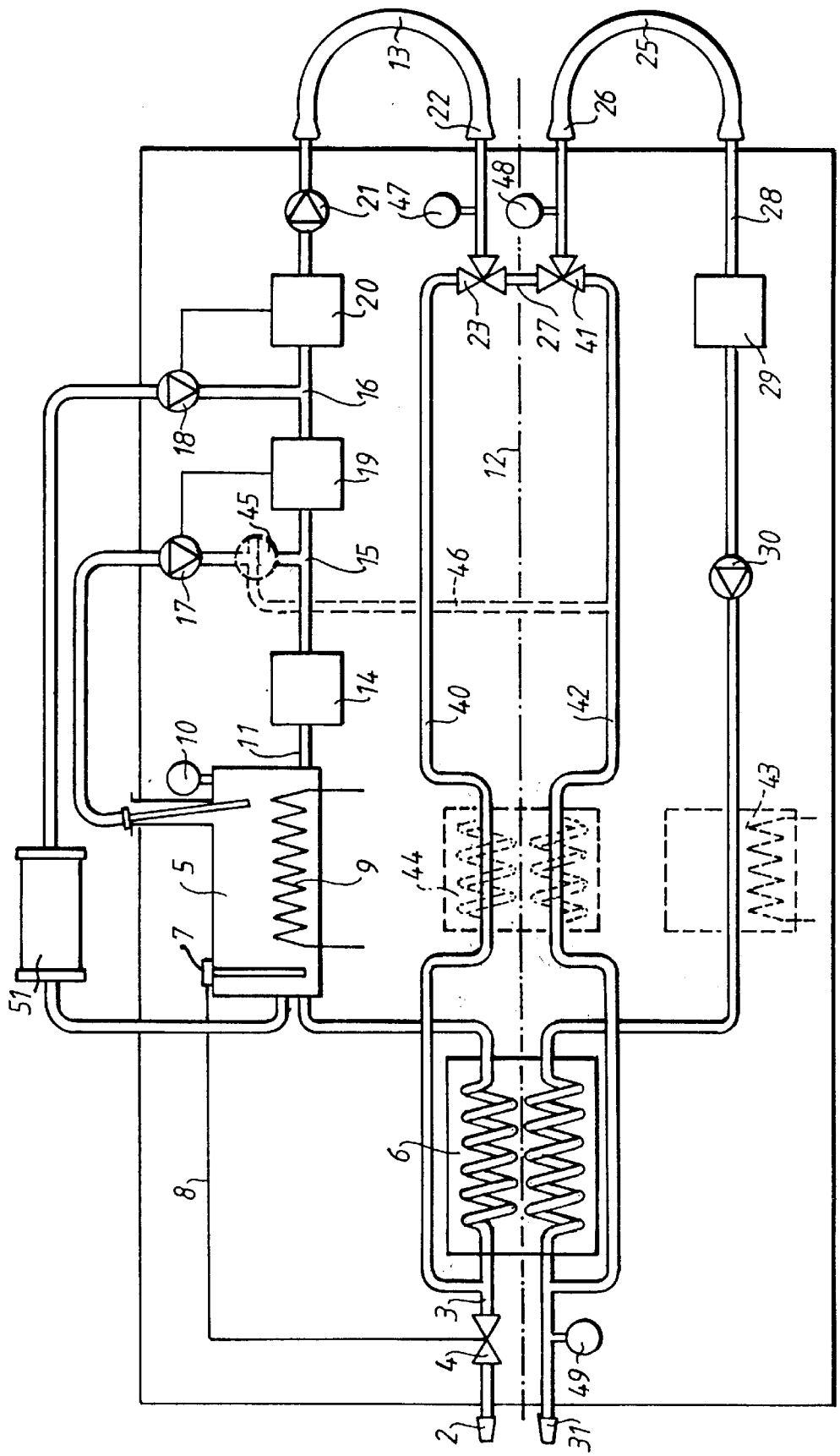
FIG. 2 is a schematic representation similar to that of FIG. 1, showing a preferred embodiment of the present invention.

From FIG. 2 it is clear that the recirculation conduit 24 in FIG. 1 has been extended and is connected with the inlet conduit 3 immediately after the inlet valve 4. In this manner, the first recirculation circuit for the clean side is extended so that the clean side is disinfected to a maximum extent. Additionally, the water passes through the heat exchanger 6 in the first circuit.

The shunt conduit 27 is provided with a recirculation valve 41, one end of which is connected with a second recirculation conduit 42, which extends from the valve 41 to just before the outlet 31. In this manner, a second recirculation circuit is formed from the tube 25 through the outlet conduit 28 and the pump 30, through the heat exchanger 6, through the second recirculation conduit 42 to the valve 41 as well as to the coupling 26 and the tube 25, as is clearly visible from FIG. 2. This second circuit has been obtained essentially by adding the valve 41 and the recirculation conduit 42.

A function of the disinfection arrangement according to FIG. 2 is as follows. The valve 23 is adjusted so that substantially all of the solution which passes through the tube 13 is diverted to the first recirculation conduit 40 and, by means of the pump 21, is circulated in the first circuit through the water vessel 5. The water in the first circuit is heated up by means of the heating coil 9. At the same time the valve 41 is adjusted so that substantially all of the fluid in the tube 25, the conduit 28, as well as the second recirculation conduit 42, is circulated by means of the pump 30 in the second circuit. Heat energy is transferred through the heat exchanger 6 from the first circuit to the second circuit for which reason the temperature also rises successively in the second circuit until a high temperature, in the area of 95° C., is reached in both circuits.

The valves 23 and 41 are adjusted (or are already positioned) so that a small amount of fluid passes through the shunt conduit 27 from the first circuit to the second circuit. In order to keep the first circuit filled, the inlet valve 4 is, at the same time, automatically opened somewhat and the water comes in through the conduit 2. At the same time surplus amounts of fluid are given off into the second circuit by means of the outlet 31.

By means of the arrangement which is described in FIG. 2, no additional heating coil is required apart from the heating coil 9 which is located in the water vessel 5, since the heat exchanger 6 is sufficiently effective in raising the temperature in the second circuit by a sufficient amount. As a complement, however, the second circuit can also be provided with an immersion heater or other heater 43 as shown with dashed lines in FIG. 2.

In certain cases it is desired to avoid the use of the heat exchanger 6 in the normal circuit in the dialysis machine, for example due to the risk of contamination of the inlet of the dialysis machine with bacteria which enters into the machine through the outlet 31. For this, the immersion heater 43 is used by itself for heating the second circuit. It is also possible to place the heat exchanger in another position, for example between the two recirculation conduits 40 and 42, as indicated with the dashed block 44 in FIG. 2.

In order to transfer a certain amount of fluid from the first circuit to the second circuit, one of the metering pumps 17 and 18 can be used instead of the valves 23 and 41, and the bypass-conduit 27, which pump transfers fluid by means of a valve 45 and a conduit 46 from the first to the second circuit, as shown by dashed lines in FIG. 2.

Since the water vessel 5 is connected with the atmosphere, the temperature therein cannot rise above 100° C. If, despite everything, this should occur, nothing serious happens apart from the water in the vessel 5 boiling and steam being given off through its connection with atmosphere. The remainder of this first circuit has a lower temperature, this also including the heat exchanger. As an extra safety measure, the first circuit has a pressure sensor 47.

The second circuit is heated by means of the heat exchanger and cannot reach a higher temperature than that of the first circuit. For additional monitoring a pressure sensor 48 is used. Especially when a heater 43 is used, there may also be a temperature sensor 49, for example at the outlet 31. These sensors are connected with a monitoring system which produces an alarm signal in the event of dangerous or incorrect conditions.

FIG. 2 shows a cartridge 51 connected in the holder which, during normal operation, contains a bicarbonate cartridge. The cartridge 51 contains citric acid and/or any other disinfection medium as is described in more detail in European Patent Application No. 458,041 (CLEANCART®). This cartridge 51 is optional, and need not be used in normal operation.

Figure 3:
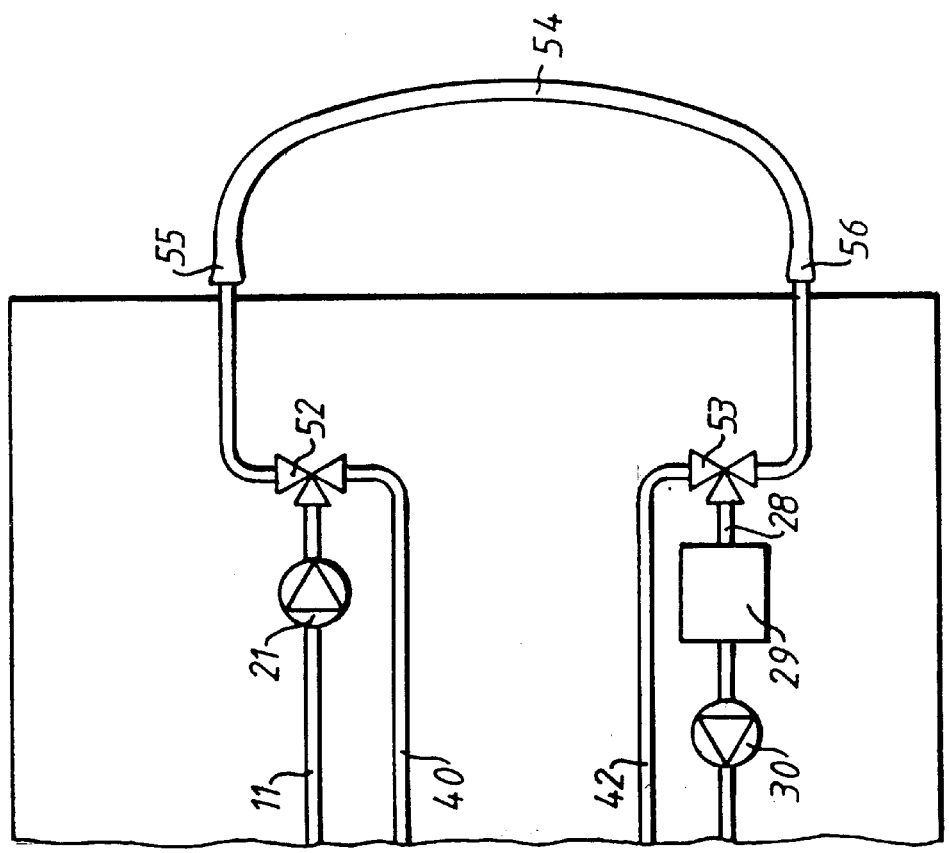
FIG. 3 is a schematic representation similar to that of FIG. 2, showing an alternative embodiment of the present invention.

Certain dialysis machines lack the bypass-conduit 27 which is replaced by a shunt conduit directly from the outlet of the supply conduit 11 to the inlet of the return conduit 28. In this case, the valves 23 and 41 are arranged in the manner shown in FIG. 3. The feed conduit 11 is provided with a three-way valve 52 corresponding to the valve 23, which directly connects the feed conduit 11 with the first recirculation conduit 40 in order to form the first circuit. Additionally, the return conduit 28 is provided with a three-way valve 53 corresponding to the valve 41, which directly connects the return conduit 28 with the second recirculation conduit 42. A shunt conduit 54 connects a feed outlet 55, where the tube 13 is normally connected, with a return inlet 56, where the tube 25 is normally connected. The shunt conduit 54 can constitute the tubes 13 and 25 coupled together, or an outer or inner shunt conduit. The operation of this embodiment is the same as described above.

Some dialysis machines have closed or substantially closed systems which allow pressure to be built up in either or both circuits. In such a case, the temperature can be raised to above 100° C., for example to 121° C., which normally means an over-pressure of about 1 atmosphere.

Preferred embodiments of the present invention have been described above with reference to the drawings. These embodiments can be modified in many ways by a skilled man upon reading this description. Such modifications which are obvious for the skilled man are intended to be encompassed within the scope of the present invention. The different parts which are described with reference to the drawings can be combined in different ways than those shown in the drawings.

We claim:

1. Apparatus for disinfection of a dialysis machine having (a) a dialysis solution supply conduit for supplying dialysis solution to a dialyzer when connected to said dialysis machine, said dialysis solution supply conduit having an inlet and an outlet and (b) a dialysis solution removal conduit for removing dialysis solution from said dialyzer when connected to said dialysis machine, said dialysis solution removal conduit having an inlet and an outlet, said apparatus comprising:

a first circulation means for disinfecting at least a portion of said dialysis solution supply conduit, said first circulation means including a first recirculation conduit having a first end connected to said inlet of said dialysis solution a first end connected to said inlet of said dialysis solution supply conduit and a second end connected to said outlet of said dialysis solution supply conduit, said first circulation means being operative to pump a first disinfecting fluid through said first recirculation conduit to circulate said first disinfecting fluid through said at least a portion of said dialysis solution supply conduit; and a second circulation means for disinfecting at least a portion of said dialysis solution removal conduit, said second circulation means including a second recirculation conduit having a first end connected to said inlet of said dialysis solution removal conduit and a second end connected to said outlet of said dialysis solution removal conduit, said second circulation means being operative to pump a second disinfecting fluid through said second recirculation conduit to circulate said second disinfecting fluid through said at least a portion of said dialysis solution removal conduit.

2. The apparatus of claim 1 wherein said second circulation means includes a second fluid heating means for heating said second disinfecting fluid.

3. The apparatus of claim 1 wherein said dialysis solution supply conduit includes a first fluid heating means for heating said first disinfecting fluid.

4. The apparatus of claim 3 including a heat exchanger for transferring heat between said first disinfecting fluid in said first circulation means and said second disinfecting fluid in said second circulation means.

5. The apparatus of claim 4 wherein said heat exchanger is operatively arranged with respect to said supply conduit and said removal conduit for transferring heat between said first disinfecting fluid in said first circulation means and said second disinfecting fluid in said second circulation means.

6. The apparatus of claim 4 wherein said heat exchanger is operatively arranged with respect to said first and second recirculation conduits to transfer heat from said first disinfecting fluid in said first circulation means to said second disinfecting fluid in said second circulation means.

7. The apparatus of claim 1 including a shunt conduit for transferring disinfecting fluid from said first circulation means to said second circulation means.

8. The apparatus of claim 1 wherein said dialysis solution supply conduit includes at least one disinfecting medium inlet for supplying a disinfecting medium to said dialysis solution supply conduit.

9. The apparatus of claim 7 wherein said shunt conduit includes a pump.

10. Apparatus for disinfection of a dialysis machine having (a) a dialysis solution supply conduit for supplying dialysis solution to a dialyzer when connected to said dialysis machine, said dialysis solution supply conduit having an inlet and an outlet and (b) a dialysis solution removal conduit for removing dialysis solution from said dialyzer when connected to said dialysis machine, said dialysis solution removal conduit having an inlet and an outlet, said apparatus comprising:
a first circulation means for disinfecting at least a portion of said dialysis solution supply conduit, said first circulation means including a first recirculation conduit having a first end connected to said inlet of said dialysis solution supply conduit and a second end connected to said outlet of said dialysis solution supply conduit, and further including a first heating means arranged with respect to said first recirculation conduit to heat disinfect fluid circulating through said first recirculation conduit, said first circulation means being operative to pump a first disinfecting fluid through said first recirculation conduit to circulate said first disinfecting fluid through said at least a portion of said dialysis solution supply conduit; and a second circulation means for disinfecting at least a portion of said dialysis solution removal conduit, said second circulation means including a second recirculation conduit having a first end connected to said inlet of said dialysis solution removal conduit and a second end connected to said outlet of said dialysis solution removal conduit, and further including a second heating means arranged with respect to said second recirculation conduit to heat disinfect fluid circulating through said second recirculation conduit, said second circulation means being operative to pump a second disinfecting fluid through said second recirculation conduit to circulate said second disinfecting fluid through said at least a portion of said dialysis solution removal conduit.

11. The apparatus of claim 10, wherein said second heating means is a heat exchanger for transferring heat from said first disinfecting fluid in said first circulation means to said second disinfecting fluid in said second circulation means.

12. The apparatus of claim 11 wherein said heat exchanger is operatively arranged with respect to said supply removal conduits to transfer heat from said first disinfecting fluid in said first circulation means to said second disinfecting fluid in said second circulation means.

13. The apparatus of claim 11 wherein said heat exchanger is operatively arranged with respect to said first and second recirculation conduits to transfer heat between said first disinfecting fluid in said first recirculation means and said second disinfecting fluid in said second recirculation means.

14. The apparatus of claim 10 including a shunt conduit for transferring disinfecting fluid from said first circulation means to said second circulation means.

15. The apparatus of claim 14 wherein said shunt conduit includes a pump.

16. The apparatus of claim 10 wherein said dialysis solution supply conduit includes at least one disinfecting medium inlet for supplying a disinfecting medium to said dialysis solution supply conduit.

17. Apparatus for disinfection of a dialysis machine having (a) a dialysis solution supply conduit for supplying dialysis solution to a dialyzer when connected to said dialysis machine, said dialysis solution supply conduit having an inlet and an outlet and (b) a dialysis solution removal conduit for removing dialysis solution from said dialyzer when connected to said dialysis machine, said dialysis solution removal conduit having an inlet and an outlet, said apparatus comprising:
a first circulation means for disinfecting at least a portion of said dialysis solution supply conduit, said first circulation means including a first recirculation conduit having a first end connected to said inlet of said dialysis solution supply conduit and a second end connected to said outlet of said dialysis solution supply conduit, said first circulation means including a first heating means arranged with respect to said first recirculation conduit to heat disinfecting fluid circulating through said first recirculation conduit, said first circulation means being operative to pump a first disinfecting fluid through said first recirculation conduit to circulate said first disinfecting fluid through said at least a portion of said dialysis solution supply conduit; and a second circulation means for disinfecting at least a portion of said dialysis solution removal conduit, said second circulation means including a second recirculation conduit having a first end connected to said inlet of said dialysis solution removal conduit and a second end connected to said outlet of said dialysis solution removal conduit, said second circulation means including a heat exchanger for transferring heat from said first disinfecting fluid in said first circulation means to said second disinfecting fluid in said second circulation means, said second circulation means being operative to pump a second disinfecting fluid through said second recirculation conduit to circulate said second disinfecting fluid through said at least a portion of said dialysis solution removal conduit.

18. The apparatus of claim 17 wherein said first heating means is arranged adjacent said inlet of said supply conduit in order to supply heated first disinfecting fluid to said supply conduit and said heat exchanger being positioned upstream of said heating means.

19. The apparatus of claim 17 wherein said heat exchanger is operatively arranged with respect to said supply and removal conduits to transfer heat from said first disinfecting fluid in said first circulation means to said second disinfecting fluid in said second circulation means.

20. The apparatus of claim 17 wherein said heat exchanger is operatively arranged with respect to said first and second recirculation conduits to transfer heat between said first disinfecting fluid in said first recirculation means and said second disinfecting fluid in said second recirculation means.

21. The apparatus of claim 17 including a shunt conduit for transferring fluid between said first circulation means and said second circulation means.

22. The apparatus of claim 21 wherein said shunt conduit includes a pump.

23. The apparatus of claim 17 wherein said dialysis solution supply conduit includes at least one disinfecting medium inlet for supplying a disinfecting medium to said dialysis solution supply conduit.

* * * * *

UNITED STATES PATENT AND TRADEMARK OFFICE
CERTIFICATE OF CORRECTION

PATENT NO. : 5,948,247
DATED : Sept. 7, 1999
INVENTOR(S) : Gillerfalk et al.

It is certified that error appears in the above-identified patent and that said Letters Patent is hereby corrected as shown below:

Column 4, line 27, delete "at: " and inset therefor --at--.
Column 6, lines 61-62, delete "a first end connected to said inlet of said dialysis solution".
Column 7, line 59, delete "disinfect" and insert therefor --disinfecting--.
Column 8, line 7, delete "disinfect" and insert therefor --disinfecting--.

Signed and Sealed this

Seventeenth Day of October, 2000

Attest:

Q. TODD DICKINSON

*Attesting Officer*      *Director of Patents and Trademarks*